United States Patent
Gajewski

(10) Patent No.: US 7,381,401 B2
(45) Date of Patent: Jun. 3, 2008

(54) T CELL ANERGY IS REVERSED BY ACTIVE RAS AND REGULATED BY DIACYLGLYCEROL KINASE

(75) Inventor: Thomas F. Gajewski, Chicago, IL (US)

(73) Assignee: The University of Chicago, Chicago, IL (US)

( * ) Notice: Subject to any disclaimer, the term of this patent is extended or adjusted under 35 U.S.C. 154(b) by 16 days.

(21) Appl. No.: 11/032,516

(22) Filed: Jan. 10, 2005

(65) Prior Publication Data
US 2005/0266510 A1    Dec. 1, 2005

Related U.S. Application Data

(60) Provisional application No. 60/535,072, filed on Jan. 8, 2004.

(51) Int. Cl.
*A61K 49/00* (2006.01)

(52) U.S. Cl. ...................................................... 424/9.2

(58) Field of Classification Search ...................... None
See application file for complete search history.

(56) References Cited

OTHER PUBLICATIONS

Chakrabarti et al. J Cellular Biochemistry 2000;78:222-230.*
Zimmermann et al. Anticancer Res 1993;13(2):347-354.*
Aussel et al. Cellular Immunology 1992;139:333-341.*
Bursell et al. Investigative Ophthalmology &Visual Science 1997;38(13:2711-2720.*
Haneda et al. Am J Kidney Diseases 2001;38(4 suppl 1):s178-181.*
Boussiotis et al., "Maintenance of human T cell anergy: blocking of IL-2 gene transcription by activated rap1," *Science*, 278:124-128, 1997.
Crespi et al., "Constitutive active p21$^{ras}$ enhances primary T cell responsiveness to Ca$^{2+}$ signals without interfering with the induction of clonal anergy," *Eur J Immunol*, 32:2500-2509, 2002.
Dower et al., "RasGRP is essential for mouse thymocyte differentiation and TCR signaling," *Nat Immunol*, 1:317-321, 2000.
Ebinu et al., "RasGRP links T-cell receptor signaling to Ras," *Blood*, 95:3199-3203, 2000.
Outram et al., "Diacylglycerol kinase α activity promotes survival of CD4$^+$ 8$^+$ double positive cells during thymocyte development," *Immunology*, 105:391-398, 2002.
Peterson et al., "T cell development and function in CrkL-deficient mice," *Eur J Immunol*, 33(10):2687-2695, 2003.
Rayter et al., "p21ras mediates control of IL-2 gene promoter function in T cell activation," *EMBO J*, 11:4549-4556, 1992.
Sanjuan et al., "Role of diacylglycerol kinase alpha in the attenuation of receptor signaling," *J. Cell Biol*, 153:207-220, 2001.
Sebzda et al., "Rap1A positively regulates T cells via integrin activation rather than inhibiting lymphocyte signaling," *Nat Immunol*, 3:251-258, 2002.
Swan et al., "Involvement of p21ras distinguishes positive and negative selection in thymocytes," *EMBO J*, 14:276-285, 1995.
Zhong et al., "Enhanced T cell responses due to diacylglycerol kinase ζ deficiency," *Nat Immunol*, 4:882-890, 2003.
Zhong et al., "Regulation of T cell receptor-induced activation of the Ras-ERK pathway by diacylglycerol kinase ζ" *J. Biol. Chem.*, 277:31089-31098, 2002.

* cited by examiner

*Primary Examiner*—Ralph Gitomer
*Assistant Examiner*—Bin Shen
(74) *Attorney, Agent, or Firm*—Fulbright & Jaworski

(57) ABSTRACT

T cell anergy has been correlated with defective Ras signaling. However, neither a causal relationship nor the mechanism of Ras hypoactivation have been established. Using adenoviral transduction of CAR Tg T cells to enable genetic manipulation in nonproliferating cells, we show that Ras61L restores IL-2 production and MAP kinase signaling in T cells anergized in vitro or in vivo. A gene array screen revealed upregulated diacylglycerol kinase (DGK) in the anergic state, which was confirmed by RT-PCR and Western blot analysis. A DGK inhibitor significantly restored IL-2 production by anergic cells. Our data support a causal role for DGK and defective Ras signaling in T cell anergy.

4 Claims, 10 Drawing Sheets

FIG. 1A-C

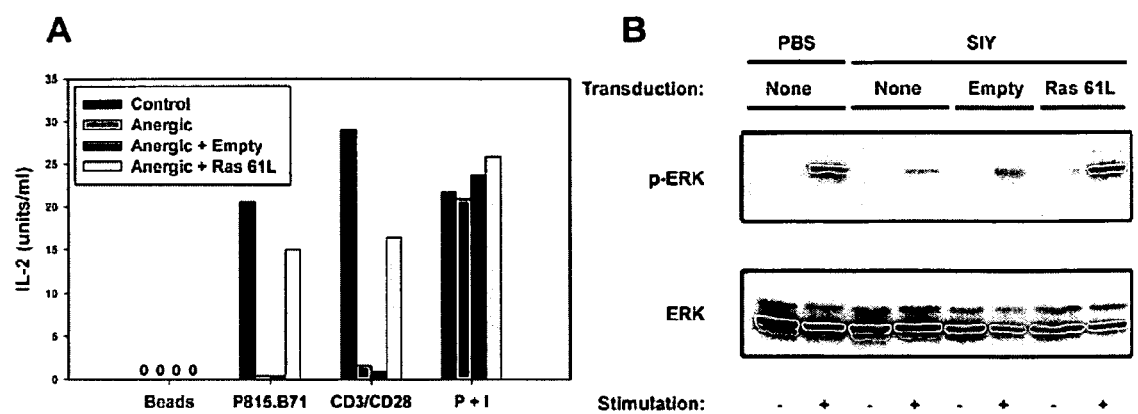
FIG. 3A-B

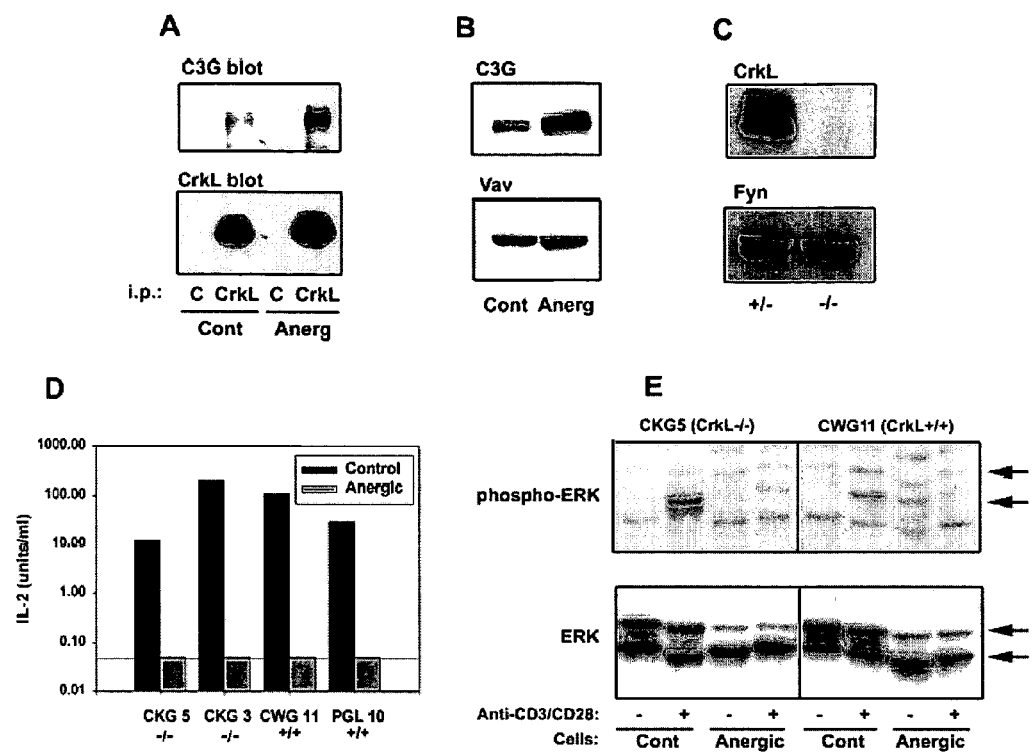
FIG. 4A-E

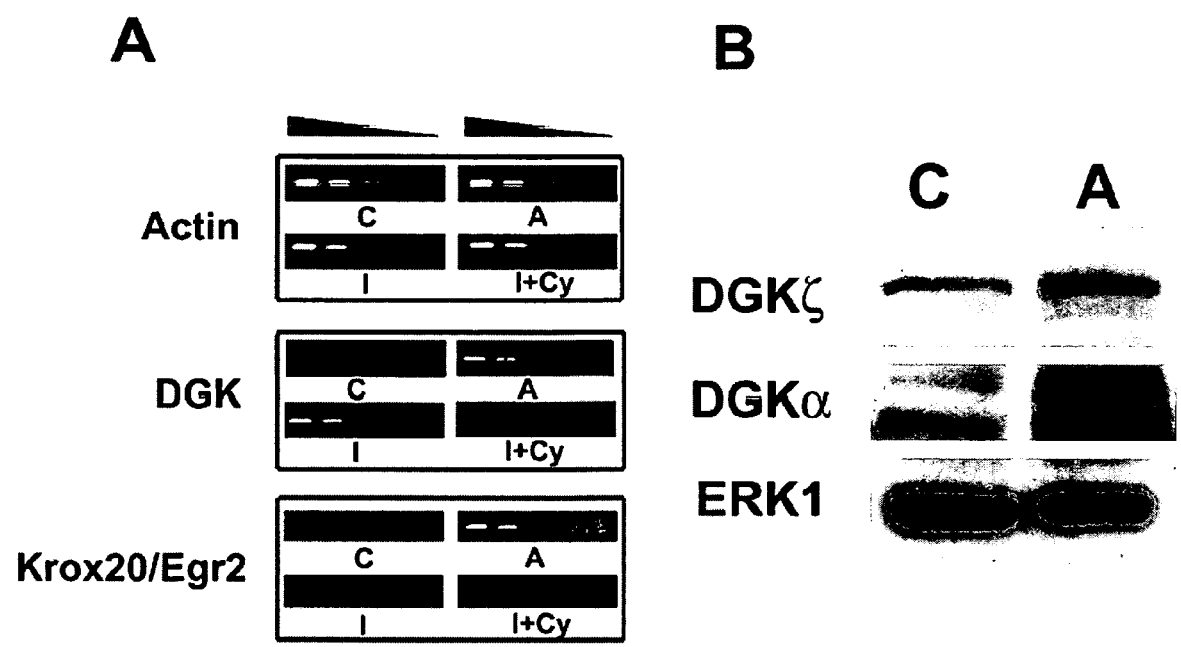
FIG. 5A-C

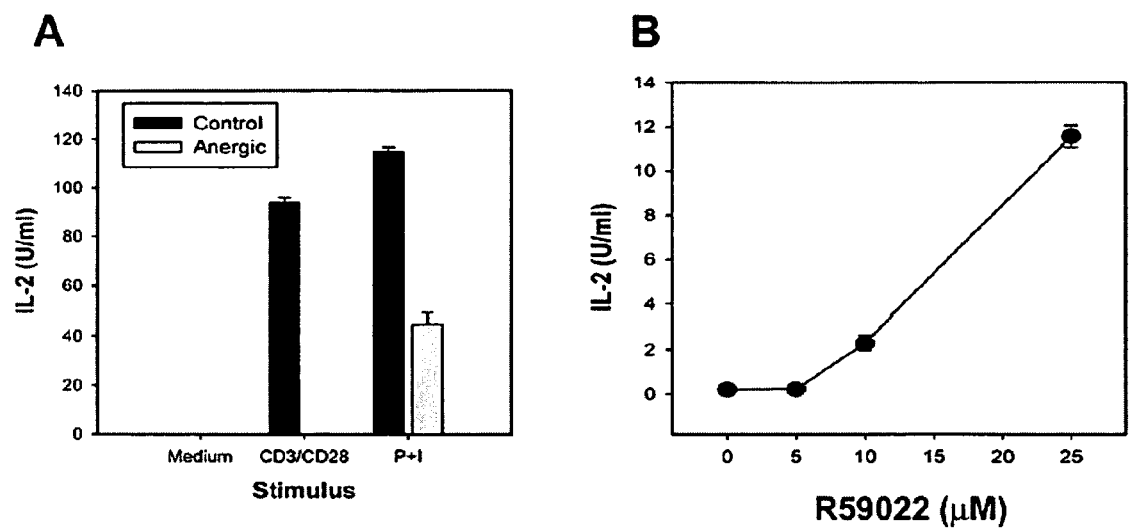
FIG. 6A-B

SEQUENCE LISTING

```
<160> NUMBER OF SEQ ID NOS: 7

<210> SEQ ID NO 1
<211> LENGTH: 39
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 1
ggccagtgaa ttgtaatacg actcactata gggaggcgg                          39

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 2
taaaacgcag ctcagtaaca gtccg                                         25

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 3
tggaatcctg tggcatccat gaaac                                         25

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 4
ttctttagga agcatttcca                                               20

<210> SEQ ID NO 5
```

```
-continued

<211> LENGTH: 19
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 5
gtagggtagg caccacatc                                                  19

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 6
ggaattccat gatgaccg                                                   18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 7
ggaattcctc acggtgtc                                                   18
```

T CELL ANERGY IS REVERSED BY ACTIVE RAS AND REGULATED BY DIACYLGLYCEROL KINASE

The present application claims the benefit of U.S. Provisional Application Ser. No. 60/535,072, filed on Jan. 8, 2004, the entire text of which is incorporated herein by reference.

This invention was made with government support under grant number R01AI7919 awarded by the National Institutes of Health. The government has certain rights in the invention.

BACKGROUND OF THE INVENTION

1. Field of the Invention

The present invention relates generally to the field of immunology. More particularly, it concerns the causal role for diacylglycerol kinase (DGK) and defective Ras signaling in T cell anergy. An implementation of the invention relates to the identification of compounds that can modulate or mimic DGK-α and/or DGK-ζ activity and the use of these compounds to treat conditions that result from immune dysregulation.

2. Description of the Related Art

Engagement of the T cell receptor for antigen (TCR) in the absence of CD28 costimulation can result in a long-term hyporesponsive state termed clonal anergy (Schwartz, 2003). Anergic T cells show defective IL-2 production and proliferation upon restimulation via the TCR and CD28, and produce other cytokines at reduced levels. Anergy may represent one mechanism of peripheral tolerance (Ramsdell et al., 1989), and has been reported to occur in the setting of non-productive anti-tumor immunity in vivo (Staveley-O'Carroll et al., 1998). Thus, understanding the regulation of induced T cell hyporesponsiveness may enable manipulation of immune responses to favor tolerance versus activation, having broad potential application toward disease states associated with immune dysregulation.

The molecular alterations in the anergic state that correlate with defective IL-2 production in response to TCR/CD28 engagement have been evaluated in some detail (Fields et al., 1996). The most compelling correlative signaling perturbation is a deficiency in Ras activation, which is associated with diminished activation of the MAP kinases ERK and JNK (Fields et al., 1996; Li et al., 1996) as well as blunted AP-1 transactivation (Kang et al., 1992). The ability of dominant negative (DN) Ras to inhibit IL-2 promoter activity in T cell tumor lines (Rayter et al., 1992) coupled with the block in thymic development seen in DN Ras transgenic mice (Swan et al., 1995) support an important role for Ras signaling in TCR-mediated T cell activation. Nevertheless, whether deficient Ras activation is sufficient to explain the anergic phenotype has not been formally demonstrated.

In part, the lack of mechanistic data regarding Ras and anergy is due to the technical limitations of current strategies for genetic manipulation of normal T cells in vitro. In particular, a key study would require introduction of constitutively active (CA) Ras into already anergized T cells, to determine if MAP kinase activation and IL-2 production could be restored. Retroviral transduction would require cell proliferation for integration and gene expression, which is not possible with growth-arrested anergic T cells. However, by utilizing T cells from Coxsackie and adenovirus receptor (CAR) transgenic mice (Wan et al., 2000), a model which enables adenoviral transduction of quiescent non-proliferating cells, the inventor shows that that introduction of CA Ras61L into resting anergic T cells restores IL-2 production and MAP kinase activation, indicating a causal role for blocked Ras in mediating the anergic state. The results are in apparent contrast with a recent report in which T cells transduced with a retrovirus encoding active Ras were still rendered hyporesponsive (Crespi et al., 2002). However, retroviral transduction required that the cells be transduced first and then anergized, and it is conceivable that early and constitutive Ras activation might itself contribute to T cell dysregulation. The experimental approach used by the inventor allowed active Ras to be introduced after anergy was induced, and in model systems in which a blockade in Ras signaling is known to occur.

Previous reports have suggested that increased recruitment of CrkL-C3G complexes and concomitant Rap1 activation might be responsible for the decreased TCR-induced Ras/MAP kinase activation and IL-2 production in anergic cells (Boussiotis et al., 1997). However, the inventor recently observed that CrkL-deficient mice generated by gene targeting do not show T cell hyperresponsiveness (Peterson et al., 2003), and the present invention shows that Th1 cells derived from CrkL-deficient mice are still capable of being anergized. In addition, recent work has shown that transgenic expression of Rap1 in T cells promotes increased T cell activation through augmented adhesion (Sebzda et al., 2002). Collectively, these results make it unlikely that CrkL-C3G and Rap1 are involved in a major negative regulatory pathway in T cells, although these molecules could conceivably dampen TCR signaling under other circumstances.

Other gene products have been reported as candidates for contributing to T cell hyporesponsiveness in the anergic state. The transcriptional regulator Tob has been found to be upregulated in anergic cells, and transfection of cells to overexpress Tob led to diminished IL-2 production (Tzachanis et al., 2001). However, Tob was also found to be highly expressed in naive T cells, and naive T cells show robust IL-2 production in response to TCR/CD28 ligation. Thus, although signals involving Tob may be important for the negative regulation of T cell activation, they do not appear to parallel the anergic phenotype. A recent report has identified GRAIL, an E3 ubiquitin ligase, as being upregulated in anergic cells and negatively regulating TCR-mediated cytokine gene expression (Anandasabapathy et al., 2003). It is conceivable that GRAIL could also antagonize Ras signaling, and/or that diminished Ras signaling could promote GRAIL upregulation.

Although previous studies correlated T cell anergy with defective Ras signaling, neither a causal relationship nor the mechanism of Ras hypoactivation had been established. Thus, a better understanding of the regulation of induced T cell hyporesponsiveness is needed to enable manipulation of immune responses to favor tolerance versus activation. The ability to manipulate the immune response would have the potential for broad application toward disease states associated with immune dysregulation.

SUMMARY OF THE INVENTION

The present invention is based on the inventor's determination that there is a causal role for blocked Ras signaling in mediating the anergic state and identifying diacylglycerol kinase (DGK)-α and -ζ as anergy-associated molecules that act upstream from Ras as negative regulators. Accordingly, the present invention provides methods for identifying compounds with the ability to manipulate the immune response by modulating or mimicking the activity of DGK-α or DGK-ζ. Compounds identified using these methods have the potential for broad application toward treating diseases associated with immune dysregulation.

In one embodiment, the invention provides a method of identifying compounds that modulate a diacylglycerol kinase (DGK) comprising contacting a cell with a test compound; and determining whether DGK activity is altered, the altered DGK activity being an indication that the test compound modulates DGK. In a preferred embodiment the DGK is DGK-α or DGK-ζ. In other preferred embodiments the cell is a T cell. In yet other preferred embodiments, the test compound is a peptide, polypeptide, polynucleotide, or small molecule. In one aspect of the invention the method of identifying compounds that modulate a diacylglycerol kinase (DGK) comprises high-throughput screening.

In certain aspects of the invention, the method of determining whether DGK activity is altered in the presence of a test compound comprises determining whether there is an increase or decrease in phosphatidic acid formation relative to the level of DGK activity in the absence of the test compound.

In yet other embodiments, the invention provides methods of identifying compounds that mimic a diacylglycerol kinase (DGK) comprising contacting a cell with a test compound; and determining whether DGK activity is increased, the increase in DGK activity being an indication that the test compound mimics DGK. In preferred embodiments the DGK is DGK-α or DGK-ζ. In other preferred embodiments the cell is a T cell. In one aspect of the invention the test compound is a peptide, polypeptide, polynucleotide, or small molecule. In certain embodiments, the method of identifying compounds that mimic a diacylglycerol kinase (DGK) comprises high-throughput screening.

In certain aspects of the invention, the method of determining whether a test compound mimics DGK activity comprises determining whether there is an increase in phosphatidic acid formation relative to the level of DGK activity in the absence of the test compound.

In another embodiment, the invention provides methods of identifying compounds that modulate T cell anergy. In a preferred embodiment, the invention provides methods of identifying compounds that modulate T cell anergy by modulating DGK activity. In another preferred embodiment, the invention provides methods of identifying compounds that modulate T cell anergy by mimicking DGK activity.

In some embodiments, the invention provides methods of identifying compounds capable of modulating the activity of a DGK comprising: contacting the DGK with a test compound; and determining whether the test compound binds to the DGK, the binding of the test compound to the DGK being an indication that the test compound is capable of modulating the activity of the DGK. In a preferred embodiment the DGK is DGK-α or DGK-ζ. In other preferred embodiments the test compound is a peptide, polypeptide, polynucleotide, or small molecule. In certain aspects of the invention, the method of identifying compounds capable of modulating the activity of a DGK comprises high-throughput screening. In a preferred embodiment, the method of determining whether the test compound binds to the DGK comprises a cell free binding assay.

In other embodiments, the invention provides methods of alleviating T cell anergy comprising contacting an anergic T cell with a compound that inhibits DGK-α or DGK-ζ. In a preferred embodiment, the compound is identified by a method comprising: contacting a cell with a test compound; and determining whether DGK-α or DGK-ζ activity is decreased, the decrease in DGK-α or DGK-ζ activity being an indication that the test compound inhibits DGK-α or DGK-ζ. In some embodiments, determining whether DGK-α or DGK-ζ activity is decreased comprises determining whether there is decrease in phosphatidic acid formation. In some aspects of the invention, the test compound is a peptide, polypeptide, polynucleotide, or small molecule. In certain embodiments, the method of identifying compounds that inhibit DGK-α or DGK-ζ comprises high-throughput screening. In other preferred embodiments, compounds that inhibit DGK-α or DGK-ζ are identified by a method comprising: contacting DGK-α or DGK-ζ with a test compound; and determining whether the test compound binds to the DGK-α or DGK-ζ, the binding of the test compound to the DGK-α or DGK-ζ being an indication that the test compound is capable of modulating the activity of the DGK-α or DGK-ζ. In a preferred embodiment, determining whether the test compound binds to the DGK-α or DGK-ζ comprises a cell free binding assay. In certain aspects the method comprises high-throughput screening.

In a preferred embodiment, the invention provides methods of inducing T cell anergy comprising contacting a T cell with a compound that mimics DGK-α or DGK-ζ.

In yet other preferred embodiments, the invention provides methods of treating a subject having a condition that would benefit from down-regulation of an immune response comprising inducing T cell anergy, wherein T cell anergy is induced by administering to the subject an effective amount of an activator or mimic of DGK-α or DGK-ζ. In one embodiment the subject is a mammal. In a preferred embodiment the mammal is a human.

In certain embodiments the condition is an autoimmune disorder, a transplant, a graft versus host disease, an allergy, or an inflammatory disorder. In preferred embodiments the autoimmune disorder is diabetes mellitus, rheumatoid arthritis, juvenile rheumatoid arthritis, osteoarthritis, psoriatic arthritis, multiple sclerosis, encephalomyelitis, myasthenia gravis, systemic lupus erythematosis, autoimmune thyroiditis, atopic dermatitis eczematous dermatitis, psoriasis, Sjogren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, or interstitial lung fibrosis.

In other embodiments the transplant is a bone marrow transplant, a stem cell transplant, a heart transplant, a lung transplant, a liver transplant, a kidney transplant, a cornea transplant, or a skin transplant.

In another preferred embodiment, the invention provides methods of treating a subject having a condition that would benefit from up-regulation of an immune response comprising alleviating T cell anergy, wherein T cell anergy is alleviated by administering to the subject an effective amount of a inhibitor of DGK-α or DGK-ζ. In one embodiment the subject is a mammal. In a preferred embodiment the mammal is a human. In one aspect of the invention, the condition cancer.

In other embodiments, the invention provides a composition comprising a diacylglycerol kinase (DGK) modulator identified by a method comprising: contacting a cell with a test compound; and determining whether DGK activity is altered, the altered DGK activity being an indication that the test compound modulates DGK. In a preferred embodiment the DGK is DGK-α or DGK-ζ. In other preferred embodiments the cell is a T cell. In certain aspects, the test compound is a peptide, polypeptide, polynucleotide, or small molecule. In some embodiments, the method of identifying a DGK modulator comprises high-throughput screening. Determining whether DGK activity is altered in the presence of a test compound may comprise determining whether there is an increase or decrease in phosphatidic acid formation. In a preferred embodiment, the DGK modulator modulates T cell anergy.

In one embodiment, the present invention provides a composition comprising a diacylglycerol kinase (DGK) mimic identified by a method comprising: contacting a cell with a test compound; and determining whether DGK activity is increased, the increase in DGK activity being an indication that the test compound mimics DGK. In a preferred embodiment the DGK is DGK-α or DGK-ζ. In other preferred embodiments the cell is a T cell. In some aspects of the invention, the test compound is a peptide, polypeptide, polynucleotide, or small molecule. The method of identifying a DGK mimic may comprise high-throughput screening. In a preferred embodiment, the method determining whether DGK activity is increased in the presence of the test compound comprises determining whether there is an increase in phosphatidic acid formation. In yet another preferred embodiment the DGK mimic modulates T cell anergy.

In another embodiment, the invention provides a pharmaceutical composition comprising: a diacylglycerol kinase (DGK) modulator identified by a method comprising: contacting a cell with a test compound, and determining whether DGK activity is altered, the altered DGK activity being an indication that the test compound modulates DGK; and at least one pharmaceutically acceptable excipient.

In still another embodiment, the invention provides a pharmaceutical composition comprising: a diacylglycerol kinase (DGK) mimic identified by a method comprising: contacting a cell with a test compound, and determining whether DGK activity is increased, the increase in DGK activity being an indication that the test compound mimics DGK; and at least one pharmaceutically acceptable excipient.

As used herein the specification, "a" or "an" may mean one or more. As used herein in the claim(s), when used in conjunction with the word "comprising", the words "a" or "an" means one or more than one. As used herein "another" may mean at least a second or more.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A shows that anergic CAR Tg T cells are efficiently transduced. Control and anergic Th1 cells were transduced with an adenoviral vector encoding GFP and analyzed by flow cytometry. The two histogram curves are superimposable.

FIG. 1B shows effective transduction with Ras61L. CAR Tg Th1 cells were transduced with an adenoviral vector encoding Ras61L (10 pfu) or with an empty vector. Lysates were analyzed by Western blotting using an antibody against H-Ras.

FIG. 1C shows that transduced anergic Th1 cells recover production of IL-2. Anergic CAR Tg Th1 cells were either left untransduced or were transduced with an empty vector or with Ras61L (10 pfu). Control cells are shown for comparison. All cells were stimulated with either empty beads, anti-CD3/anti-CD28 beads, or with PMA+Ionomycin (P+I). Supernatants were collected at 18 hr and assessed for IL-2 content by ELISA.

FIGS. 3A and 3B. Transduction of in vivo anergized CAR Tg CD8+2C T cells with Ras61L restores IL-2 production and MAP kinase signaling. CAR Tg 2C/RAG2$^{-/-}$ mice were treated with SIY peptide to induce anergy in vivo. T cells were harvested and either left untransduced or were transduced with an empty vector or with Ras61L (10 pfu). Control cells from PBS-treated mice were used for comparison. In FIG. 3A, cells were stimulated with either empty beads, P815.B71 cells, anti-CD3/anti-CD28 beads, or PMA+ionomycin (P+I); supernatants were collected 18 hours later and assessed for IL-2 content by ELISA. In FIG. 3B, cells were stimulated with either empty beads or anti-CD3/anti-CD28 beads for 20 minutes and assayed for phospho-ERK and total ERK by Western blotting.

FIGS. 4A, 4B, 4C, 4D, and 4E. Increased CrkL-C3G complexes are dispensable for anergy induction. In FIG. 4A, the Th1 clone pGL10was either unmanipulated (Cont) or anergized with anti-CD3 mAb (Anerg). Immunoprecipitation was done with either control rabbit antiserum (C) or with anti-CrkL. Western blotting was performed against C3G (upper panel) or CrkL (lower panel).

In FIG. 4B, whole cell lysates from the study in FIG. 4A were blotted with anti-C3G (upper panel) or anti-Vav as a control (lower panel). In FIG. 4C, wildtype and CrkL-deficient Th1 clones were analyzed by Western blotting for CrkL (upper panel) and for Fyn as a control (lower panel). In FIG. 4D, wildtype and CrkL-deficient Th1 clones were either left unmanipulated or anergized with anti-CD3 mAb. Cells were then stimulated with anti-CD3/anti-CD28 beads and IL-2 production was measured after 18 hr.

In FIG. 4E, the indicated CrkL-deficient and wildtype Th1clones were either left unmanipulated or anergized with anti-CD3 mAb. Cells were then stimulated with either empty beads or with anti-CD3/anti-CD28 beads for 20 minutes, then analyzed by Western blotting for phospho-ERK (upper panel) and total ERK (lower panel).

FIGS. 5A and 5B. Confirmatory screens for genes upregulated in anergic T cells. In FIG. 5A, pGL10cells either left unmanipulated (C), anergized with anti-CD3 mAb (A), anergized with ionomycin (I), or treated with ionomycin and Cyclosporin A (I+Cy) were sources of total RNA for cDNA synthesis. Semi-quantitative RT-PCR was performed with primers specific for α-actin, DGK-ζ, Egr2, and neurogranin.

Serial 3-fold dilutions of cDNA are shown. FIG. 5B shows control and anergic pGL10cells analyzed by Western blotting for DGK-ζ, DGK-α, and β-Actin.

FIGS. 6A and 6B. A DGK inhibitor partially restores IL-2 production by anergic Th1 cells. In FIG. 6A, the Th1 clone pGL10was either left unmanipulated (control) or anergized with anti-CD3 mAb (anergic). Cells were stimulated with culture medium, anti-CD3/anti-CD28 beads, or PMA and ionomycin (P+I), and IL-2 content was measured by ELISA after 18 hr.

In FIG. 6B, the anergic cells from FIG. 6A were stimulated with anti-CD3/anti-CD28 beads in the presence of increasing concentrations of the DGK inhibitor R59022. Cells were pre-incubated with the drug for 25 minutes prior to stimulation, and IL-2 production was measured by ELISA. The inhibitor alone did not induce detectable cytokine release (data not shown).

DESCRIPTION OF ILLUSTRATIVE EMBODIMENTS

A. Ras Signaling in T Cells

Figure 1:
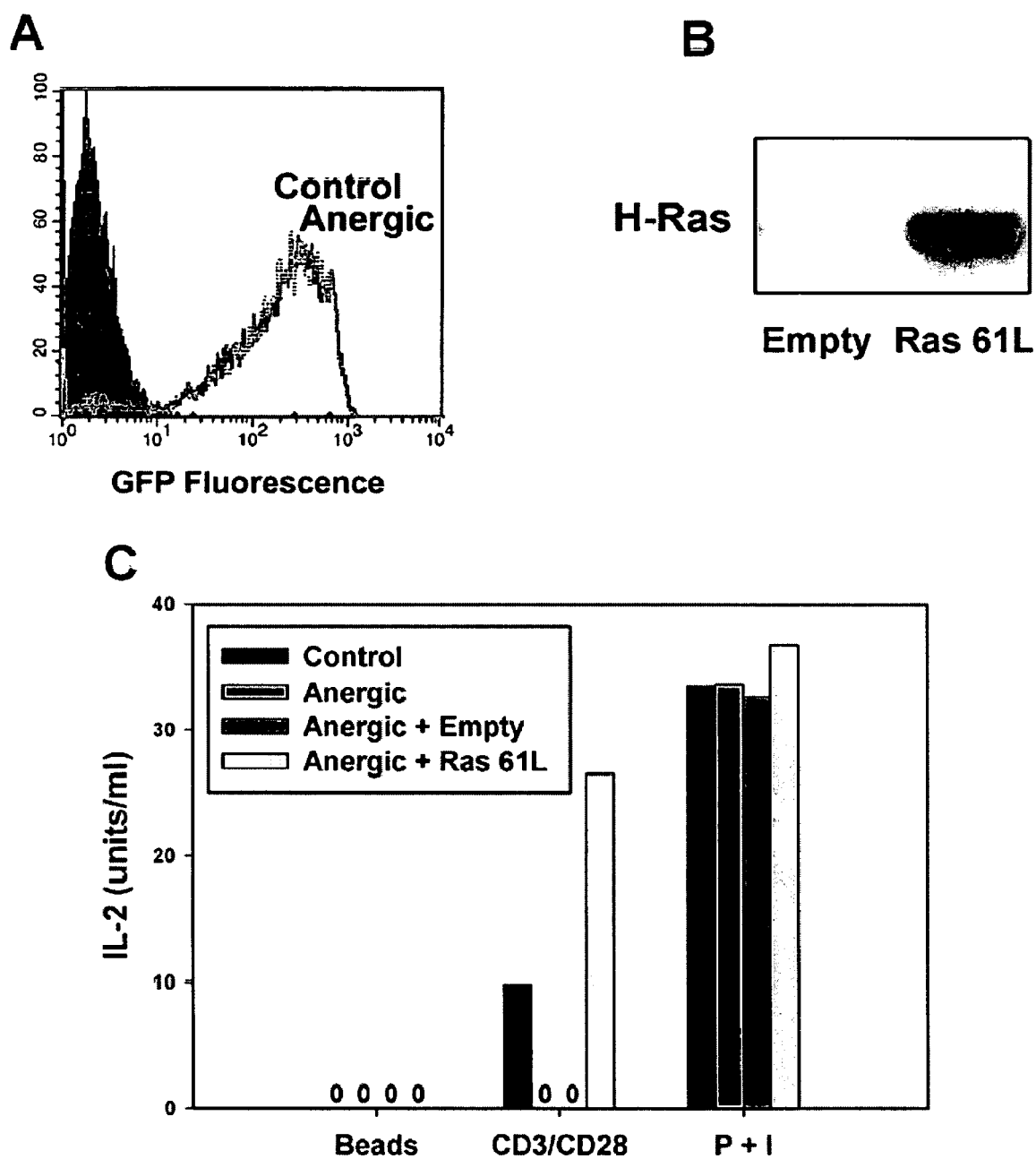
FIGS. 1A, 1B, and 1C. An adenoviral vector encoding CA Ras61L restores IL-2 production in anergic CAR Tg Th1 cells.

The identification of RasGRP as a key guanine nuclear exchange factor for Ras in T cells uncovered a mechanism by which PMA or DAG can mediate Ras activation via a relatively direct pathway (Ebinu et al., 2000; Dower et al., 2000). By depleting available DAG, increased DGK activity would block this route of Ras activation. At least 9 isoforms of DGK have been identified in the literature, and both DGK-α and DGK-ζ have been reported to be expressed in T cells (Zhong et al., 2002; Sanjuan et al., 2001; Outram et al., 2002). Forced overexpression of DGK-ζ has been shown to inhibit TCR-induced Ras/ERK activation and AP-1 reporter activity in Jurkat cells (Zhong et al., 2002), arguing that DGK-ζ can be sufficient to inhibit T cell activation. The present invention shows that upregulated expression of DGK-α and DGK-ζ correlate with the anergic state, and that a pharmacologic inhibitor of DGK partially recovers IL-2 production by anergic T cells. Of note, the DGK inhibitor did not fully restore IL-2 production to baseline levels. This agent is preferential for DGK-α, and thus likely incompletely blocks other DGK isoforms. In addition, higher concentrations of the drug were toxic, suggesting the possibility that DGK may have other functions in T cells. A recent report describing DGK-ζ-deficient mice showed increased sensitivity of TCR-mediated T cell activation (Zhong et al, 2003). Those results are consistent with the inventor's and support an important negative regulatory role for DGK in T cell activation. Further dissection of the inhibitory effect of DGK subtypes in T cell signaling may require conditional deletion in post-thymic T cells of each expressed isoform, alone and in combination.

The inventor has demonstrated that the blockade in Ras signaling in T cell anergy causally contributes to the hyporesponsive state. In addition, the inventor has identified members of the DGK family as anergy-associated genes that are strong candidates for the down-regulation of TCR-induced Ras activation. The development of selective pharmacologic agents that either mimic or modulate the activity of individual DGK isoforms could lead to new ways to regulate T cell responses either positively or negatively in vivo. In certain embodiments, the present invention provides methods for identifying compounds with the ability to manipulate the immune response by modulating or mimicking the activity of DGK isoforms such as DGK-α or DGK-ζ. Compounds identified using the methods of the present invention may be used in treating diseases associated with immune dysregulation.

B. Screening for Modulators and Mimics of Diacylglycerol Kinase Activity

The present invention provides methods for identifying modulators and mimics of DGK activity. The screening assays may comprise random screening of large libraries of test compounds. Alternatively, the assays may be used to focus on particular classes of compounds selected with an eye towards structural attributes that are believed to make them more likely to modulate or mimic DGK activity. Thus, the screening assays will assay for increases or decreases in levels of DGK function in response to a test compound. By function, it is meant that one may assay for any protein-related biological activity, such as an increased/decreased enzyme activity. Those skilled in the art are familiar with methods for assaying for DGK activity. For example, one may assay the conversion of DAG to phosphatidic acid. Alternatively, one may assay for a test compound's ability to bind to a DGK polypeptide.

As used herein the term "test compound" refers to any molecule that may potentially modulate or mimic DGK activity. The test compound may be a protein or fragment thereof, a small molecule, or even a nucleic acid molecule. Test compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the compounds identified by the present invention may be peptide, polypeptide, polynucleotide, small molecule inhibitors or any other compounds that may be designed through rational drug design starting from known inhibitors or stimulators.

One may acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled on active, but otherwise undesirable compounds.

1. Inhibitors, Activators, and Mimics

Compounds that inhibit DGK-α and/or DGK-ζ activity would be useful in the up-regulation of the immune response. Such compounds could be used in pharmaceutical compositions for the treatment of conditions, such as cancer, that would benefit from the up-regulation of an immune response. Compounds that increase DGK-α and/or DGK-ζ activity or that mimic DGK-α and/or DGK-ζ activity would be useful in the down-regulation of the immune response. Such compounds could be used in pharmaceutical compositions for the treatment of conditions such as autoimmune disorders, transplants, graft versus host disease, allergies, and inflammatory disorders. It may prove to be the case that the most useful pharmacological compounds will be compounds that are structurally related to DGK-α or DGK-ζ.

There are several known DGK inhibitors, such as R59022 and R59949 (de Chaffoy de Courcelles et al., 1985; Nunn et al., 1987; de Chaffoy de Courcelles et al, 1989). It may prove to be the case that the most useful pharmacological compounds will be compounds that are structurally related to these inhibitors. Those of skill in the art will be able to identify these structurally related compounds.

The structure of R59022 (6-[2-(4-[(4-fluorophenyl)phenyl-methylene]-1-piperidinyl)ethyl]-7-methyl-5H-thiazolo [3,2-]pyrimidine-5-one) is provided below:

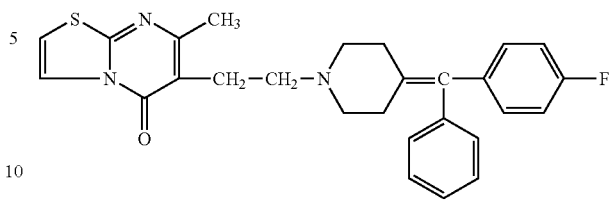

The structure of R59499 (3-[2-[4-(bis(4-fluorophenyl) methylene)-1-piperidinyl]ethyl]-2,3-dihydro-2-thioxo-4 (1H)-quinazolinone (R59499)) is provided below:

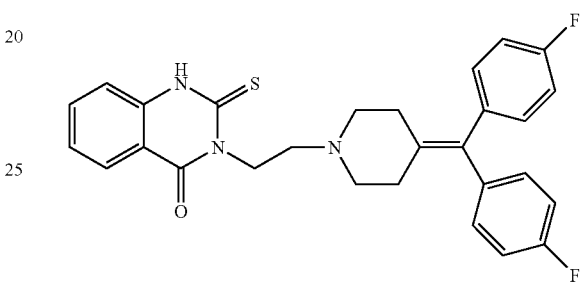

Other known modulators of DGK activity include dioctanoylglycerol; ceramide (Younes, et al., 1992); phosphatidic acid (Walsh et al., 1995); phosphatidylcholine (Thomas and Glomset, 1999); phosphatidylinositol 4,5-bisphosphate (PIP2) (Walsh et al., 1995); phosphatidylserine (Kanoh et al., 1992; Sakane et al., 1989; Lemaitre et al, 1990); rhoA (Houssa et al., 1999); sphingosine (Previati et al., 1994; Kanoh et al., 1992; Sakane et al., 1989); stemphone (Nobe et al., 2004).

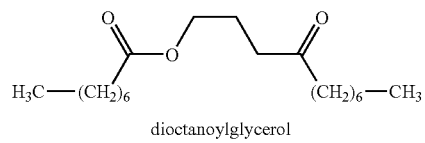
dioctanoylglycerol

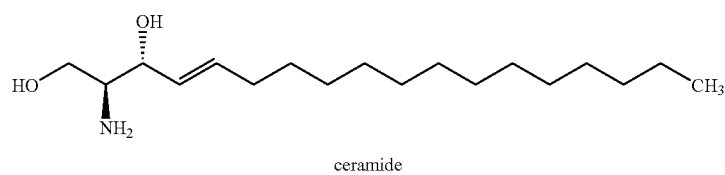
ceramide

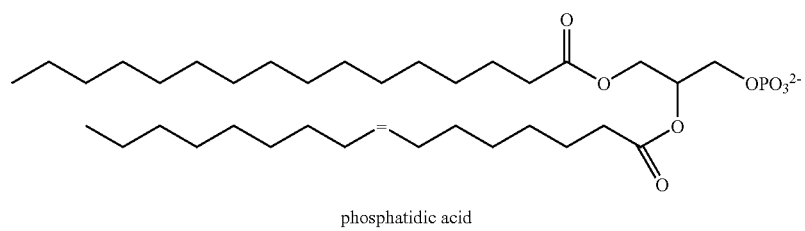
phosphatidic acid

-continued

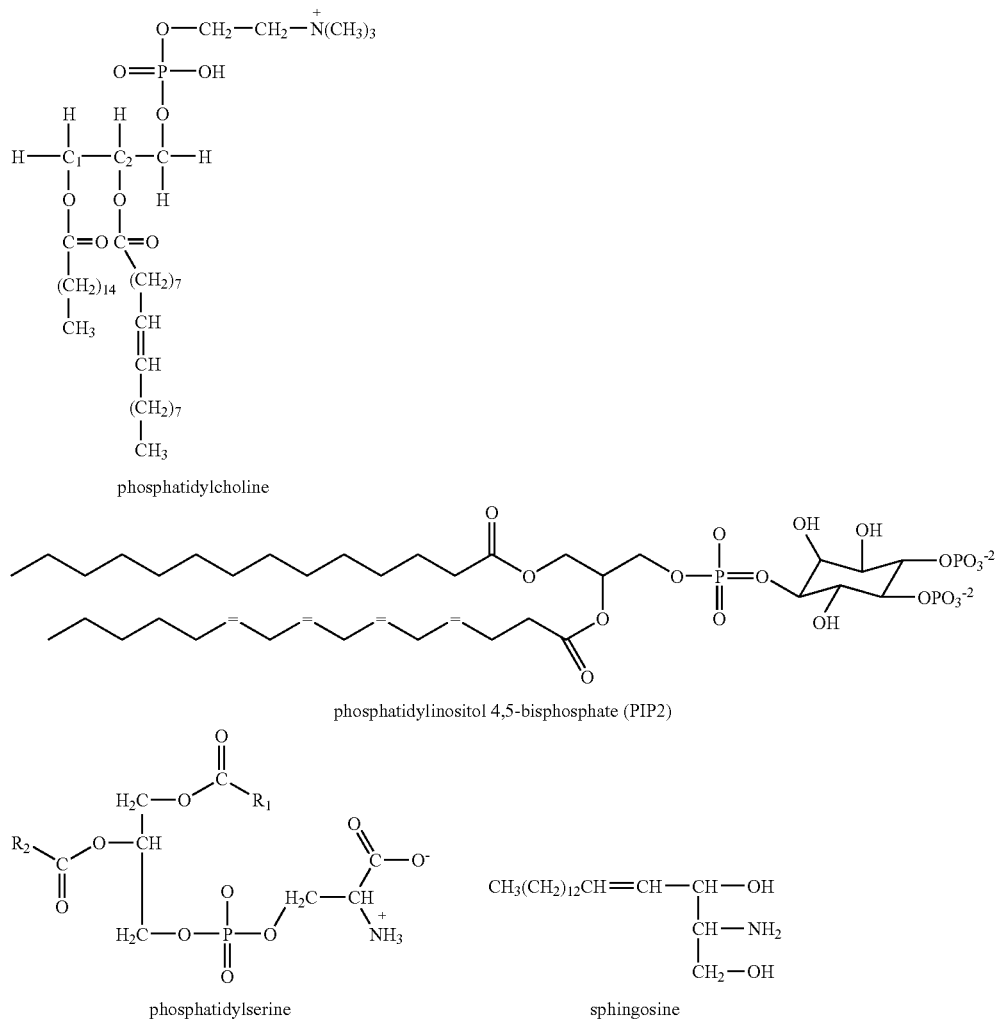

phosphatidylcholine phosphatidylinositol 4,5-bisphosphate (PIP2)

phosphatidylserine sphingosine

The crystal structure of the human RhoA protein is known in the art (Wei, 1997). The structure of stemphone is also known in the art (Huber, 1975).

Dominant-negative DGK-α mutant proteins and dominant-negative DGK-ζ mutant proteins can inhibit the wild-type DGK-α and DGK-ζ proteins. Other suitable inhibitors include antisense molecules, ribozymes, and antibodies (including single chain antibodies), each of which would be specific for the target molecule. For example, an antisense molecule that bound to a translational or transcriptional start site, or splice junctions, would be a candidate inhibitor.

3. In Vitro Assays

A quick, inexpensive and easy assay to run is an in vitro assay. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

One example of a cell free assay is a binding assay. The ability of a modulator to bind to a target molecule in a specific fashion is strong evidence of a related biological effect. For example, binding of a molecule to an enzyme may block the catalysis of a substrate. The interaction may be due to steric, allosteric or charge-charge interactions. The protein or protein complex may be either free in solution, fixed to a support, expressed in or on the surface of a cell. Either the protein or the compound may be labeled, thereby permitting determining of binding. Usually, the protein will be the labeled species, decreasing the chance that the labeling will interfere with or enhance binding. Competitive binding formats can be performed in which one of the agents is labeled, and one may measure the amount of free label versus bound label to determine the effect on binding.

A technique for high throughput screening of compounds is described in WO 84/03564. Large numbers of small peptide test compounds are synthesized on a solid substrate, such as plastic pins or some other surface. Bound polypeptide is detected by various methods.

d. In Vivo Assays

In vivo assays for DGK-α or DGK-ζ activity are well known to those of skill in the art. For example, one method is to assay the conversion of DAG to phosphatidic acid in a cell. In a preferred embodiment, DGK-α or DGK-ζ activity is assayed in a T cell. In one aspect, in vivo assays are used to identify compounds that modulate or mimic DGK-α or DGK-ζ activity. In such assays, the cell is contacted with one or more test compounds, and the ability of the test compound(s) to alter DGK activity are determined, as compared to a similar cell not treated with the test compound(s). The ability of a test compound to alter DGK activity as compared to a non-treated cell identifies a modulator or mimic.

The invention also contemplates in vivo studies involving various animal models to further characterize compounds identified as modulators or mimics of DGK activity. Animal models include transgenic animals that have been engineered to have specific defects, or carry markers that can be used to measure the ability of a compound to reach and effect different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for modulators may be conducted using an animal model derived from any of these species.

In such assays, one or more test compounds are administered to an animal, and the ability of the test compound(s) to modulate or mimic DGK-α or DGK-ζ activity, as compared to a similar animal not treated with the test compound(s), identifies a modulator or mimic. In addition to DGK-α or DGK-ζ activity, one may also measure other characteristics. These characteristics may be a change with regard to a particular protein, e.g., changes in IL-2 production, changes in ERK activation or JNK activation, or changes in AP-1 transactivation; or instead a broader indication such as T cell proliferation, T cell anergy, or an altered immune response.

Treatment of animals with test compounds will involve the administration of the compound, in an appropriate form, to the animal. Administration will be by any route that could be utilized for clinical or non-clinical purposes, including but not limited to oral, nasal, buccal, or even topical. Alternatively, administration may be by intracerebral, intratracheal instillation, bronchial instillation, intradermal, subcutaneous, intramuscular, intraperitoneal or intravenous injection. Specifically contemplated routes are systemic intravenous injection, regional administration via blood or lymph supply, or directly to an affected site.

Determining the effectiveness of a compound in vivo may involve a variety of different criteria. One of ordinary skill in the art would be familiar with a wide range of techniques for assaying T cell activation or T cell anergy, whether the subject is an animal or a human subject. Also, measuring toxicity and dose response can be performed in animals in a more meaningful fashion than in in vitro or in cyto assays.

C. Rational Drug Design

Whatever the structure or the nature of the compounds identified by the methods of the present invention one can use the identified compounds to further develop compounds for therapeutic uses. Using lead compounds to help develop improved compounds is known as "rational drug design" and includes not only comparisons with know inhibitors, activators, and mimics, but predictions relating to the structure of target molecules.

The goal of rational drug design is to produce structural analogs of biologically active polypeptides or other compounds (e.g., small molecules). By creating such analogs, it is possible to fashion drugs, which are more active or stable than the natural molecules, which have different susceptibility to alteration or which may affect the function of various other molecules. In one approach, one would generate a three-dimensional structure for a target molecule, or a fragment thereof. This could be accomplished by x-ray crystallography, computer modeling or by a combination of both approaches.

It also is possible to use antibodies to ascertain the structure of a target compound activator or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

In addition to the modulating or mimicking compounds initially identified, the inventor also contemplates that other sterically similar compounds may be formulated to mimic the key portions of the structure of the modulators. Such compounds, which may include peptidomimetics of peptide modulators, may be used in the same manner as the initial modulators.

D. Clinical Trials

This section is concerned with the development of human treatment protocols for providing therapy for conditions involving immune dysregulation using the modulators and mimics of DGK-α and/or DGK-ζ activity identified by the methods of the invention as described herein. Candidates for the phase 1 clinical trial will be patients on which all conventional therapies have failed. The modulators and mimics of DGK-α and/or DGK-ζ activity described herein will be administered. Tests that will be used to monitor the progress of the patients and the effectiveness of the treatments include: physical exam, X-ray, blood work and other clinical laboratory methodologies. The doses given in the phase 1 study will be escalated as is done in standard phase 1 clinical phase trials, i.e. doses will be escalated until maximal tolerable ranges are reached. Clinical responses may be defined by acceptable measure. For example, a complete response may be defined by complete disappearance of the disease or condition, whereas a partial response may be defined by a 50% reduction of the disease or condition. The typical course of treatment will vary depending upon the individual patient and disease being treated in ways known to those of skill in the art.

E. Immunodetection Methods

The present invention also concerns immunodetection methods for binding, purifying, removing, quantifying or otherwise generally detecting biological components. The steps of various useful immunodetection methods have been described in the scientific literature, such as, e.g., Nakamura et al. (1987; incorporated herein by reference). Immunoassays, in their most simple and direct sense, are binding assays. Certain preferred immunoassays are the various types of enzyme linked immunosorbent assays (ELISAs), radioimmunoassays (RIA) and immunobead capture assay. Immunohistochemical detection using tissue sections also is particularly useful. However, it will be readily appreciated that detection is not limited to such techniques, and Western blotting, dot blotting, FACS analyses, and the like also may be used in connection with the present invention.

In general, the detection of immunocomplex formation is well known in the art and may be achieved through the application of numerous approaches. These methods are generally based upon the detection of a label or marker, such as any radioactive, fluorescent, biological or enzymatic tags or labels of standard use in the art. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

F. Pharmaceutical Preparations

Pharmaceutical compositions of the present invention comprise an effective amount of one or more modulators or mimics of DGK-α and/or DGK-ζ activity identified as described by the present invention dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one modulator or mimic of DGK-α and/or DGK-ζ activity will be known to those of skill in the art in light of the present disclosure, as exemplified by Remington's Pharmaceutical Sciences, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, antioxidants, salts, coatings, surfactants, preservatives (e.g., methyl or propyl p-hydroxybenzoate, sorbic acid, antibacterial agents, antifungal agents), isotonic agents, solution retarding agents (e.g. paraffin), absorbents (e.g. kaolin clay, bentonite clay), drug stabilizers (e.g. sodium lauryl sulphate), gels, binders (e.g. syrup, acacia, gelatin, sorbitol, tragacanth, polyvinylpyrrolidinone, carboxy-methyl-cellulose, alginates), excipients (e.g. lactose, milk sugar, polyethylene glycol), disintegration agents (e.g. ager-ager, starch, lactose, calcium phosphate, calcium carbonate, alginic acid, sorbitol, glycine), wetting agents (e.g. cetyl alcohol, glycerol monostearate), lubricants, absorption accelerators (e.g. quaternary ammonium salts), edible oils (e.g. almond oil, coconut oil, oily esters or propylene glycol), sweetening agents, flavoring agents, coloring agents, fillers, (e.g. starch, lactose, sucrose, glucose, mannitol, silicic acid), tabletting lubricants (e.g. magnesium stearate, starch, glucose, lactose, rice flower, chalk), carriers for inhalation (e.g. hydrocarbon propellants), buffering agents, or such like materials and combinations thereof, as would be known to one of ordinary skill in the art (see, for example, Remington's Pharmaceutical Sciences, 1990). Except insofar as any conventional carrier is incompatible with the active ingredient, its use in the therapeutic or pharmaceutical compositions is contemplated.

In any case, the composition may comprise various antioxidants to retard oxidation of one or more component. Examples of antioxidants includes ascorbic acid, cysteine hydrochloride, sodium sulfite, sodium bisulfite, sodium metabisulfite, ascorbyl palmitate, butylated hydroxytoluene, butylaed hydroxyanisole, lecithin, propyl gallate, and -tocopherol. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof).

The modulators and mimics of DGK-α and/or DGK-ζ activity may be formulated into a composition in a free base, neutral or salt form. Pharmaceutically acceptable salts include the acid addition salts, e.g., those formed with the free amino groups of a proteinaceous composition or which are formed with inorganic acids such as for example, hydrochloric, hydrobromic, or phosphoric acids; or such organic acids as acetic, oxalic, tartaric, benzoic, lactic, phosphorific, citric, maleaic, fumaric, succinic, tartaric, napsylic, clavulanic, stearic, or mandelic acid. Salts formed with the free carboxyl groups can also be derived from inorganic bases such as for example, sodium, potassium, ammonium, calcium magnesium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

The modulators and mimics of DGK-α and/or DGK-ζ activity may also comprise different types of carriers depending on whether it is to be administered in solid or liquid form, and whether it need to be sterile for such routes of administration as injection. The present invention can be administered orally, intradermally, subcutaneously, topically, by injection, infusion, continuous infusion, localized perfusion, bathing target cells directly, via a catheter, via a lavage, or by other methods or any combination of the forgoing as would be known to one of ordinary skill in the art (see, for example, Remington's Pharmaceutical Sciences, 1990).

The modulators and mimics of DGK-α and/or DGKζ activity when administered orally may be in the form of tablets, capsules, sachets, vials, powders, granules, lozenges, reconstitutable powders, liquid preparations. The modulators and mimics of DGK-α and/or DGK-ζ activity may be administered via transdermal delivery using a skin-patch formulation. The modulators and mimics of DGK-α and/or DGK-ζ activity may be dispersed in a pressure sensitive adhesive which adheres to the skin such that it can diffuse through the skin for delivery to the patient. Transdermal adhesives such as natural rubber or silicone are known in the art.

Sterile injectable solutions are prepared by incorporating the active compounds in the required amount in the appropriate solvent with various of the other ingredients enumerated above, as required, followed by filter sterilization. Generally, dispersions are prepared by incorporating the various sterilized active ingredients into a sterile vehicle that contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The actual dosage amount of a composition of the present invention administered to a patient can be determined by physical and physiological factors such as body weight, gender, severity of condition, the type of disease being treated, previous or concurrent therapeutic interventions, idiopathy of the patient, time of the administration, rate of excretion of the particular compound, and on the route of administration. The practitioner responsible for administration will, in any event, determine the concentration of active ingredient(s) in a composition and appropriate dose(s) for the individual subject. The dosage will also depend upon the bioavailability and activity of the particular modulator or mimic of DGK-α and/or DGK-ζ activity.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLE 1

Materials and Methods

Mice and cell lines. Transgenic (Tg) mice expressing the extracellular domain of the Coxsackie/adenovirus receptor (CAR) under control of the Lck promoter/CD2 enhancer cassette have been described (Wan et al., 2000). These were interbred with 2C/RAG2$^{-/-}$ mice (Manning et al., 1997). Mice were maintained under specific pathogen-free conditions in a barrier facility at the University of Chicago. CARTg or CrkL-deficient Th1 clones generated in our laboratory by immunization with ovalbumin (OVA) have been described (Wan et al., 2000) and were maintained by weekly passage as previously reported (Gajewski et al., 1989). P815.B71 cells that express $L^d$ and were transfected to express B7-1 were maintained as described (Fields et al., 1998).

Induction of T cell anergy. In vitro, Th1 cells were anergized by stimulation with plate-bound anti-CD3 Ab for 24-48 hr, harvested, and rested in culture medium alone for 24-72 hr as described (Gajewski et al., 1995). Alternatively, anergy was induced by exposure to Ionomycin (0.5 μM) or in the presence of Cyclosporin A (50 ng/ml)(Gajewski et al., 1995). In vivo anergy induction of 2C cells by administration of SIYRYYGL (SIY) peptide was performed as described (Frauwirth et al., 2001).

Adenoviral vectors. The CA H-Ras mutant Ras61L cDNA was provided by Dr. F. Fitch (University of Chicago). Construction of recombinant adenoviral vectors was performed using a two-cosmid system protocol described by Wang et al. (2000). Briefly, a gene expression unit containing a human ubiquitin promoter and either HRas61L, GFP, DGKα, kinase-dead DGKα, DGKζ, or no cDNA was inserted into a left-end plasmid, pLEP. pLEPUb-Ras61L and the right-end-plasmid, pREP, containing the E-deleted adenovirus type 2 (Ad2) genome, were digested, ligated and resulting cosmids were packaged into lambda phages. The DGKα kinase-dead DGKα, and DGKζ inserts also have a myc epitope tag. Competent bacteria were transduced with lambda phages and double selection of growing colonies was performed on Amp/Tet plates. Recombinant adenoviruses were then generated by transfection of 293 cells with purified, linearized adenoviral vector DNA. High titer stock solutions were obtained by large-scale infection of 293 cells followed by cesium chloride purification of complete viral particles. Plaque forming units (pfu) of virus preparations were determined by TCID 50 method (AdEasy Vector Systems Manual, Quantum Biotechnologies, Canada). Working solutions of adenoviral vectors were diluted in storage buffer (Nyberg-Hoffman and Aguilar-Cordova, 1999), and stored at −80° C. until needed.

Adenoviral transduction of CARTg T cells. Th1 clones were purified from passage cultures by Ficoll-Hypaque centrifugation. Primary CARTg/2C/RAG2$^{-/-}$ CD8$^+$ T cells were isolated from splenocytes by negative selection using magnetic beads and antibody cocktails (Stem Cell Technologies, Vancouver, Canada). CARTg T cells were transduced using adenoviral vectors at a multiplicity of infection (MOI) of 10 at high cell density ($10^7$ cells/ml) in 2% FCS/DMEM and incubated for 1 hr at 37° C., followed by overnight resting in 5% FCS/DMEM at 37° C. at low cell density ($4 \times 10^6$ cells/ml).

Flow cytometry. Purified T cells transduced with adeno-GFP were analyzed using a FACScan flow cytometer interfaced with an Apple computer. 10,000 events were acquired, and data were analyzed using CellQuest software.

T cell activation. T cells were activated using beads (Dynal, Oslo, Norway) coated with anti-CD3 mAb (145-2C11) and anti-CD28 mAb (PV1) as previously described (Rivas et al., 2001). Cytokine production was determined using $10^5$ T cells stimulated in microtiter plates for 18 hr at 37° C., followed by IL-2 ELISA of culture supernatant using Ab pairs obtained from BD PharMingen (San Diego, Calif.). As a control, cells were stimulated with PMA (50 ng/ml) and Ionomycin (0.5 μM). In some experiments, cells were incubated in the presence of R59022 (Sigma).

Gene array analysis. RNA was extracted from either pGL10cells anergized with plate-bound anti-CD3 mAb for 24 hr followed by a 48 hr rest period, or from control pGL10 cells harvested from passage cultures. In a second study, the control mRNA was extracted from pGL10 cells placed in culture medium alone for 72 hr. Total RNA was isolated from purified T cells. T cells were first subjected to Ficoll-Hypaque centrifugation to remove dead cells. Viable cells were isolated and washed before being lysed in Trizol® (Invitrogen, Grand Island, N.Y.). Total RNA was then treated with DNase I, (Invitrogen, Grand Island, N.Y.) to minimize contamination from genomic DNA. Further purification was carried out using the RNeasy® Clean-Up protocol (Qiagen, Valencia, Calif.).

Biotin-labeled in vitro transcripts for hybridization of Affymetrix oligonucleotide arrays were prepared from 10 µg of total RNA according to Affymetrix protocols. Briefly, cDNA was made with the SuperScript™ Choice System (Life Technologies, Grand Island, N.Y.) using 1 µl of 110 µM oligo dT/T7 primer (5'-GGCCAGTGAATTGTAATAC-GACTCACTATAGGGAGGCGG-(dT)24) (SEQ ID NO:1). The double stranded cDNA was extracted with Phenol: Chloroform:Isoamyl alcohol, precipitated with 0.5 volumes of 7.5 M Ammonium acetate and 2.5 volumes of 100% Ethanol. In vitro transcription with biotin-labeled ribonucleotides was performed with the ENZO BioArray High Yield RNA Transcript Labeling Kit (Enzo Diagnostics, New York, N.Y.). Labeled in vitro transcripts were purified over RNeasy® mini columns (Qiagen, Valencia, Calif.). 20 mg of cRNA were fragmented in a fragmentation buffer (40 mM Tris-Acetate, pH 8.1, 100 mM KOAc, 30 mM MgOAc) for 35 min at 94° C. 12 µg of fragmented cRNA was used to hybridize with each Affymetrix array according to manufacturer's instructions.

The acquisition and initial quantification of array images were performed using Affymetrix Microarray Suite Version 5.0 with default analytic parameters. The average intensity for each chip was scaled to the arbitrary value of 500 to allow comparisons among the various chips. Subsequent data analysis involved 3 steps: 1) evaluation of hybridization quality; 2) two-step data filtration: the first step was to filter genes with a signal intensity <100, and the second step was to remove gene scored as "absent"; and 3) identification of differentially expressed genes. The genes with an average ratio of greater than 2.5-fold were considered as significant and ranked according to the magnitude of differential expression.

RT-PCR. Total RNA was extracted using Trizol, and cDNA was generated using oligo-dT as a primer. PCR™ was done with titrated doses of cDNA using primers specific for the following genes:

```
β-Actin forward:
5'-TAAAACGCAGCTCAGTAACAGTCCG-3'    (SEQ ID NO:2)

β-Actin reverse:
5'-TGGAATCCTGTGGCATCCATGAAAC-3'    (SEQ ID NO:3)

DGK-ζ forward:
5'-TTCTTTAGGAAGCATTTCCA-3'         (SEQ ID NO:4)

DGK-ζ reverse:
5'-GTAGGGTAGGCACCACATC-3'          (SEQ ID NO:5)

Krox20 forward:
5'-GGAATTCCATGATGACCG-3'           (SEQ ID NO:6)

Krox20 reverse:
5'-GGAATTCCTCACGGTGTC-3'           (SEQ ID NO:7)
```

Between 36 and 39 cycles were performed at an annealing temperature of 55° C. Products were visualized on ethidium bromide-stained 1% agarose gels.

Western blotting. Cells were lysed in 0.5% Triton X-100 lysis buffer, and cleared lysates were boiled in 5× reducing sample buffer as described (Rivas et al., 2001). Protein separation was achieved using SDS-PAGE (10% or 12% gels) and transfer onto PVDF membranes (Millipore, Bedford, Mass.), and Western blotting was performed as described (Rivas et al., 2001). Immunoprecipitation with anti-CrkL or control rabbit antiserum was performed as described (Gajewski et al., 2001). Antibodies against the following proteins were obtained as indicated: phospho-ERK, phospho-JNK (Promega, Madison, Wis.); ERK (Zymed, San Francisco, Calif.); JNK1 (BD PharMingen); H-Ras, Fyn, Vav, C3G, CrkL, and DGK-ζ (Santa Cruz Biotechnologies, Santa Cruz, Calif.); and DGK-α (kind gift of H. Kanoh, Sapporo, Japan).

EXAMPLE 2

Introduction of Ras61L Restores IL-2 Production and MAP Kinase Signaling in Anergic Th1 Cells Anergic Th1 cells have been reported to show blunted activation of Ras and of the putative downstream kinases ERK and JNK. In order to determine whether defective Ras signaling was contributing to the anergic state, it was desirable to introduce CA Ras into anergic T cells and assess whether IL-2 production and MAP kinase activation were restored. However, technologic limitations had precluded genetic manipulation of non-proliferating normal T cell populations. To circumvent this issue the inventor utilized T cells from CAR Tg mice, which are transducible at high efficiency in the absence of cell proliferation using adenoviral vectors (Wan et al., 2000). To design viral vectors suitable for expression in primary T cells, the inventor screened a series of promoters and found that the human ubiquitin C (UbC) promoter (Schaefer et al., 2001) gave 1-2 logs greater expression in quiescent T cells compared to other common promoters. Ovalbumin-specific Th1 clones were generated from these mice that retained expression of CAR (Wan et al., 2000). Both control and anergic CAR Tg Th1 cells were equivalently transduced with an adenoviral vector encoding GFP driven by the UbC promoter (FIG. 1A). An empty control adenovirus did not transfer green fluorescence (data not shown). A recombinant adenovirus encoding CA Ras61L was generated using this promoter and gave high levels of Ras expression in CAR Tg Th1 cells compared to endogenous levels (FIG. 1B).

Th1 cells generated from CAR Tg mice were stimulated with immobilized anti-CD3 mAb, rested, and restimulated with either anti-CD3+anti-CD28 mAbs or PMA+Ionomycin. These cells were found to have markedly diminished IL-2 production in response to receptor ligation but still responded to PMA+Ionomycin (FIG. 1C), consistent with T cell anergy (Fields et al., 1996). Biochemical analysis confirmed decreased phosphorylation of ERK and JNK following TCR/CD28 crosslinking (FIG. 2A-B).

Figure 2:
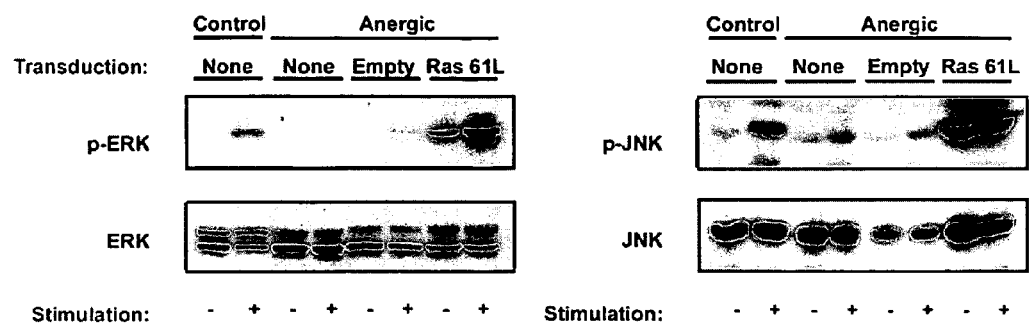
FIG. 2. Transduction with Ras61L restores MAP kinase signaling in anergic Th1 cells. Anergic CAR Tg Th1 cells were either left untransduced or were transduced with an empty vector or with Ras61L (10 pfu). Control cells are shown for comparison. All cells were stimulated with either empty beads or anti-CD3/anti-CD28 beads for 20 min. Western blotting was performed for phospho-ERK and total ERK (left panel) and for phospho-JNK and total JNK1 (right panel).

In order to determine whether active Ras would rescue normal T cell function, anergic CAR Tg Th1 cells were transduced with either an empty adenovirus or the CA Ras61L adenovirus. As shown in FIG. 1C, introduction of Ras61L but not the control vector resulted in vigorous IL-2 production by anergic cells. This cytokine production was not constitutive but required TCR engagement, consistent with Ras effectors not being sufficient for all signals leading to cytokine gene expression. Moreover, in anergic cells transduced with Ras61L, phosphorylation of ERK and JNK was restored (FIG. 2).

Thus, active Ras can restore IL-2 production and reverse the defective ERK and JNK phosphorylation seen in anergic Th1 cells.

EXAMPLE 3

CA Ras61L Restores Function of CD8+ TCR Tg T Cells Anergized In Vivo

In order to examine whether a similar signaling block was responsible for anergy induced in vivo, and to confirm this phenomenon in CD8+ T cells, CAR Tg/2C TCR Tg/RAG2$^{-/-}$ mice were generated. T cells from these mice expressed high levels of CAR and showed a transduction efficiency of 80-90% using adenoGFP (data not shown). Administration of the K$^b$-binding peptide SIYRYYGL (SIY) to 2C mice has been shown to result in T cell hyporesponsiveness (Frauwirth et al., 2001). The inventor confirmed that T cells from CARTg/2C/RAG2$^{-/-}$ mice treated with SIY peptide were defective at IL-2 production when restimulated in vitro with P815.B71 cells or with anti-CD3/anti-CD28 mAbs (FIG. 3A). However, when in vivo anergized CARTg/2C/RAG2$^{-/-}$ T cells were transduced with Ras61L prior to restimulation in vitro, IL-2 production was restored (FIG. 3A), whereas an empty adenoviral vector had no effect.

Like CD4+ Th1 clones anergized in vitro, CARTg/2C/RAG2$^{-/-}$ T cells rendered anergic in vivo showed diminished phosphorylation of ERK upon restimulation in vitro (FIG. 3B). However, ERK activation was restored following transduction with Ras61L but not with an empty vector. Thus, defective Ras signaling appears to be causally linked to the anergic state of CD8+ T cells rendered hyporesponsive in vivo.

EXAMPLE 4

Anergy of Th1 Cells does not Depend on Increased CrkL-C3G Complexes

The anergic state is thought to require production of a new protein as it is prevented by the presence of cycloheximide (Gajewski et al., 1995), and heterokaryon fusion studies have shown that anergy is in part mediated by a dominant suppressive factor (Telander et al., 1999). A leading model is that anergy is mediated by increased recruitment of CrkL-C3G complexes to the membrane via Cb1, resulting in activation of the alternative Ras-family GTPase Rap1 (Boussiotis et al., 1997). Rap1 activation has been shown to antagonize Ras-pathway signaling (Lin et al., 2000), which could explain the anergic phenotype, but also has other effects. The inventor confirmed that Th1 cells anergized with plate-bound anti-CD3 mAb showed increased levels of C3G that co-immunoprecipitated with CrkL (FIG. 4A). This appeared to be due to increased total C3G as detected by Western blotting of whole cell lysates (FIG. 4B).

In order to assess whether the increase in CrkL-C3G complexes was required for T cell anergy, OVA-specific Th1 clones were generated from CrkL-deficient mice (Peterson et al., 2003). Absence of CrkL was confirmed by Western blot analysis (FIG. 4C) and despite a lack of CrkL, these cells produced IL-2 (FIG. 4D) and IFN-γ (date not shown). Surprisingly, exposure of CrkL-deficient Th1 cells to immobilized anti-CD3 mAb successfully rendered them anergic as assessed by IL-2 production following restimulation with anti-CD3/anti-CD28 mAb (FIG. 4D). Moreover, blunted ERK phosphorylation still occurred in these anergic cells despite the absence of CrkL (FIG. 4E). These results demonstrate that CrkL is not absolutely required for the induction or maintenance of T cell anergy, and imply that anergy can occur without increased CrkLC3G recruitment.

EXAMPLE 5

Anergic Th1 Cells Express Increased Levels of Several Genes Including Diacylglycerol Kinase The lack of requisite participation of CrkL-C3G in mediating the functional or biochemical defects in anergic Th1 cells led to a search for new candidate genes upregulated in anergic cells that encoded proteins that could negatively regulate Ras activation. Replicate Affymetrix gene array screens were performed comparing RNA from resting control and anergic Th1 cells using gene chips representing 11,000 mouse genes. The results of this analysis revealed 87 genes that were expressed at increased levels in anergic cells. Ten attractive candidates among this list are shown in Table 1.

TABLE 1

Increased expression of attractive candidate genes observed in anergic Th1 cells by Affymetrix gene array analysis. Two replicate studies were performed with similar results. The mean fold-increase for both studies is shown.

| Gene | Fold increase | Accession # |
|---|---|---|
| MDR | 2.7 | AF022908 |
| DGK | 2.8 | AF085219 |
| IL-2R | 2.9 | M26271 |
| Ras-GAP-like | 4.1 | AF086714 |
| EGR2 | 5.3 | M24377 |
| Schlafen2 | 8.3 | AF099973 |
| Neurogranin | 11.3 | AI841709 |
| VAMP5 | 19.7 | AF035643 |
| CD6 | 222 | U37543 |
| CRTAM | 315 | AF001104 |

Among these genes were two candidates that encoded molecules that could theoretically negatively regulate Ras activation, a Ras-GAP-like sequence and diacylglycerol kinase (DGK)-ζ. Confirmatory analysis by semi-quantitative RT-PCR revealed that DGK-ζ mRNA was upregulated in anergic cells (FIG. 5A) whereas the RasGAP-like mRNA was not (data not shown).

DGK molecules phosphorylate DAG to generate phosphatidic acid, thus eliminating the availability of DAG to activate downstream effectors (van Blitterswijk and Houssa, 1999). The alternative guanine nucleotide exchange factor for Ras characterized in T cells, RasGRP, is directly activated by DAG in response to TCR ligation (Ebinu et al., 2000; Dower et al., 2000). Thus, expression of increased DGK-ζ might be expected to diminish Ras activation mediated by RasGRP (Topham and Prescott, 2001).

Additional conditions were used to solidify the correlation of increased DGK with anergy. Anergy is induced by elevation of intracellular calcium alone and is prevented by Cyclosporin A (Gajewski et al., 1995). As anticipated, the inventor observed that expression of DGK-ζ mRNA was upregulated by ionomycin, and this upregulation was prevented by Cyclosporin A (FIG. 5A). β-actin mRNA was relatively constant under these conditions. An additional candidate identified by gene array was similarly examined. Krox20/Egr2 is a transcriptional regulator that may negatively regulate IL-2 gene expression (Powell et al., 1999). Although increased Egr2 mRNA was observed in cells anergized by anti-CD3, only a minimal increase was observed in response to Ionomycin (FIG. 5A).

To confirm increased expression of DGK-ζ in anergic T cells at the protein level, isoform-specific antibodies were employed by Western blot analysis. At least 2 DGK isoforms, DGK-ζ and DGK-α are thought to be expressed in T-lineage cells (Zhong et al., 2002; Sanjuan et al., 2001). In fact, both isoforms appeared to be expressed at higher levels in anergic cells, with DGK-α showing the greatest increase (FIG. 5B). Thus, DGK-α and -ζ are anergy-associated molecules.

EXAMPLE 6

The DGK Inhibitor R59022 Partially Restores IL-2 Production by Anergic Th1 Cells If increased DGK activity is contributing to diminished Ras activation and IL-2 production in the anergic state, then inhibition of this enzyme should result in increased IL-2 production by anergic cells. To explore this possibility, the pharmacologic inhibitor R59022 was employed (Jiang et al., 2000). As shown in FIG. 6A, anergic Th1 cells rendered anergic by anti-CD3 mAb in vitro showed defective IL-2 production. Approximately 40% of this IL-2 production was recovered by stimulation with PMA+Ionomycin, arguing that that proportion was mediated by a proximal signaling defect. In fact, the addition of R59022 to anergic cells stimulated with anti-CD3+anti-CD28 mAb also resulted in a significant recovery of IL-2 production in a dose-dependent fashion (FIG. 6B). Higher concentrations of this agent were toxic to the cells (data not shown). These results suggest a causal role for increased DGK expression and/or function in contributing to the defect in IL-2 production characteristic of T cell anergy.

EXAMPLE 7

Overexpression of DGK Isoforms Mimics the Anergic State

Figure 7A:
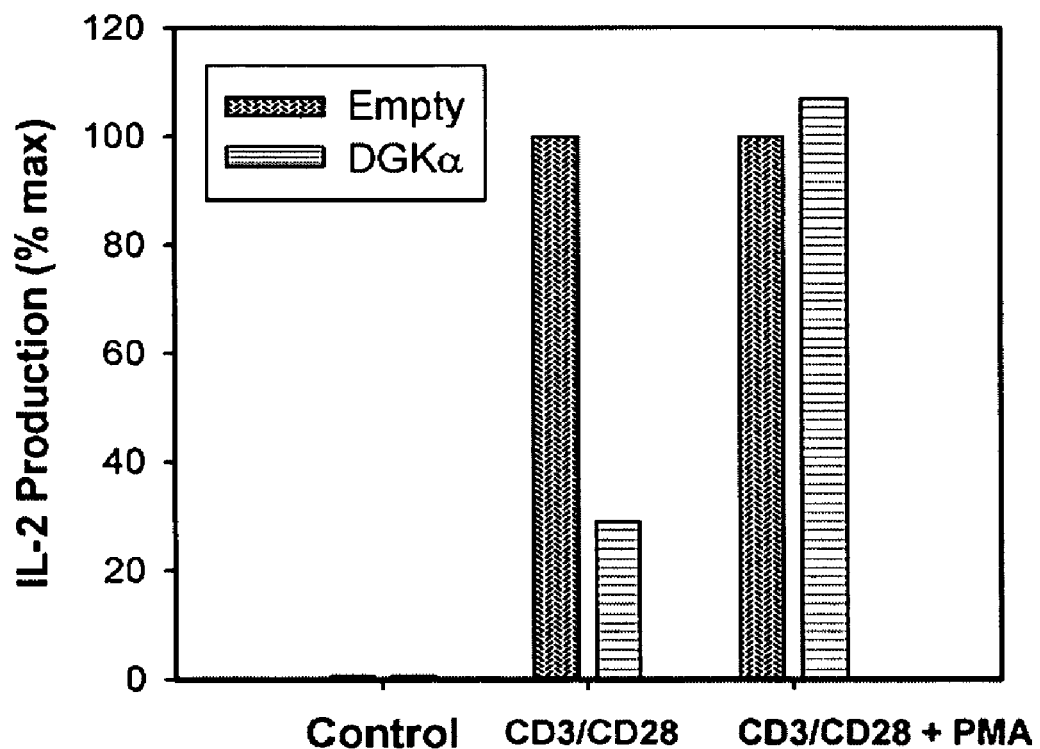
FIGS. 7A and 7B. Overexpression of DGKα in Th1 CAR Tg Clones. Introduction of DGKα significantly inhibited IL-2 production (FIG. 7A). The addition of exogenous PMA restored IL-2 production in cells transduced to express DGKα (FIG. 7A). Introduction of DGKα also led to blunted induction of phospho-ERK and phospho-JNK (FIG. 7B).
Figure 7B:
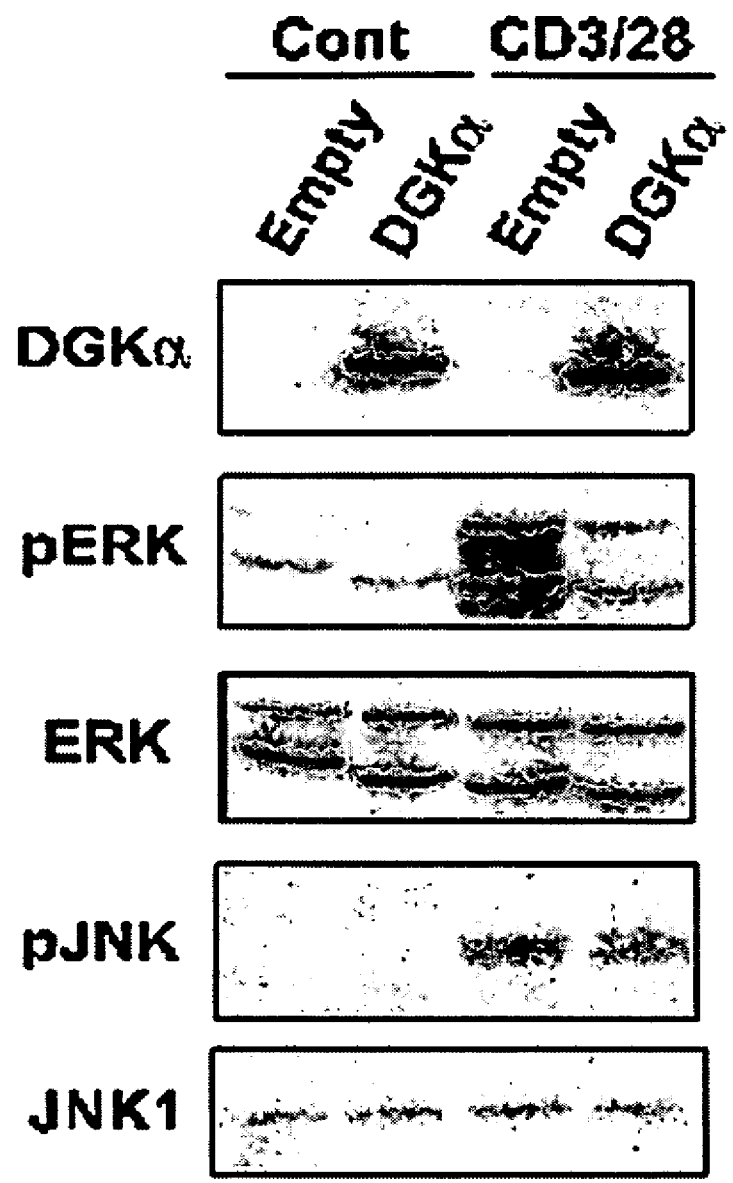

Adenoviral vectors encoding wildtype DGKα and DGKζ driven by the Ubiquitin promoter were used to transduce CAR transgenic Th1 clones, to determine whether increased expression of DGKs can mimic the anergic state. Both inserts contain a myc epitope tag. As shown in FIGS. 7A and 7B, introduction of DGKα significantly inhibited IL-2 production and also led to blunted induction of phospho-ERK and phospho-JNK. Introduction of DGKζ also inhibited IL-2 production (FIG. 8).

Figure 8:
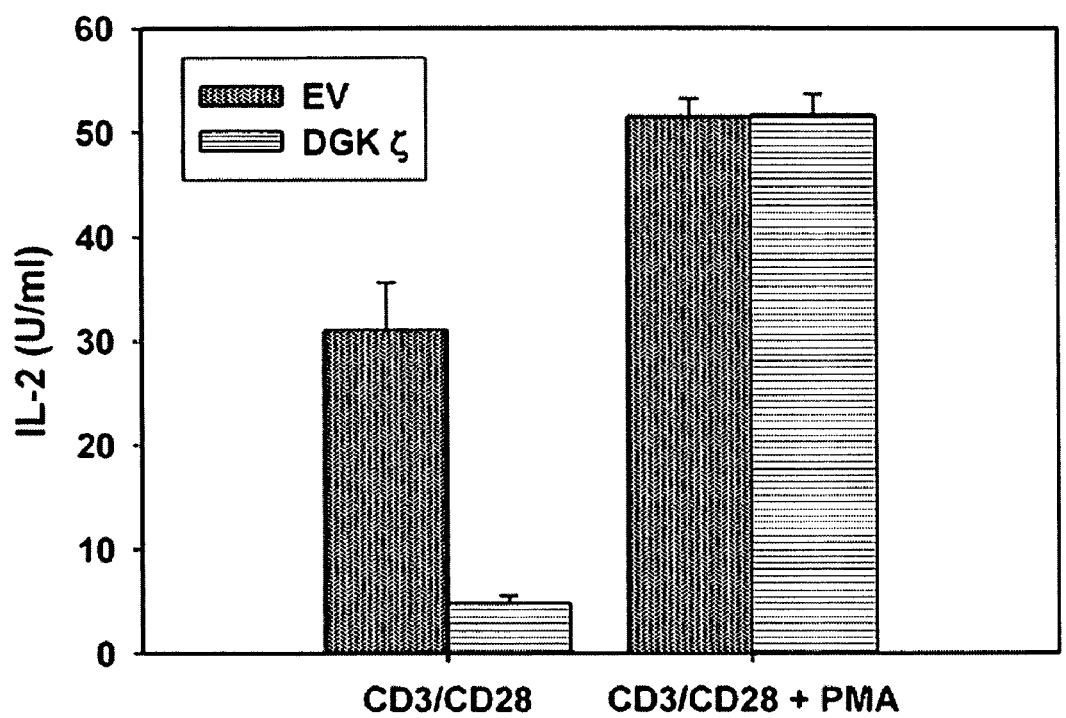
FIG. 8. Overexpression of DGKζ in Th1 CAR Tg Clones. Introduction of DGKζ inhibited IL-2 production (FIG. 8). The addition of exogenous PMA restored IL-2 production in cells transduced to express DGKζ (FIG. 8).

The addition of exogenous PMA restored IL-2 production in the cells transduced to express DGKα (FIG. 7A) and DGKζ (FIG. 8). This indicates that the overexpression of DGKs is creating a DAG-deficient environment that can be corrected with the DAG analog PMA.

EXAMPLE 8

Kinase-Dead DGKζ and R59022 Restore IL-2 Production in T Cells

Figure 9:
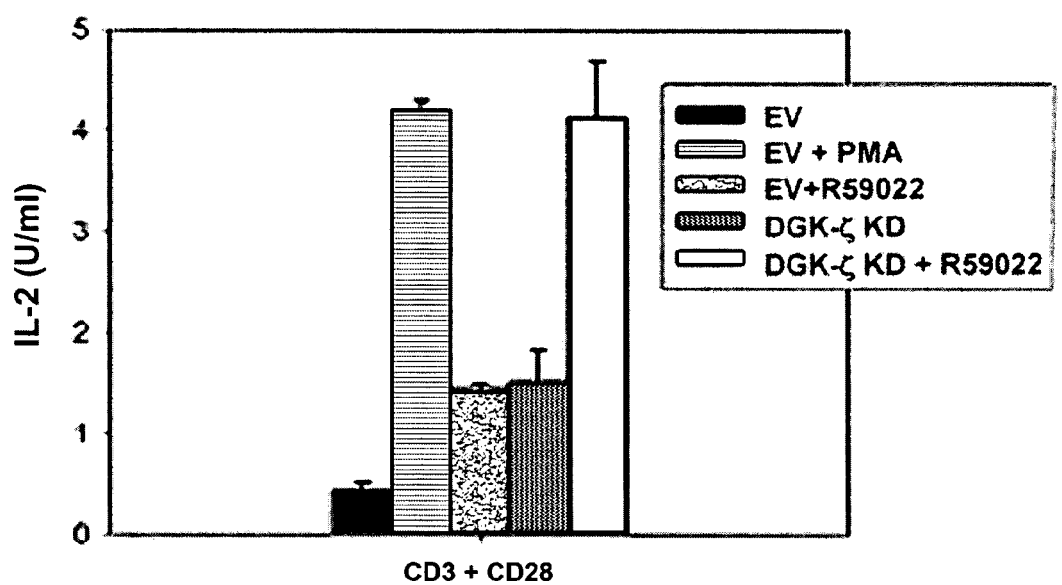
FIG. 9. Kinase-Dead DGKζ and R59022 Restore IL-2 Production in Th1 CAR Tg Clones. Introduction of kinase-dead DGKζ partially restored IL-2 production from anergic CAR Tg Th1 cells, as did the DGK inhibitor R59022 (FIG. 9). The combination of kinase-dead DGKζz and R59022 restored IL-2 production up to the level seen with exogenous PMA (FIG. 9).

An adenoviral vector encoding kinase-dead DGKζ used to transduce CAR transgenic Th1 clones, to determine if the anergic state could be reversed by inhibition of endogenous DGK activity. As shown in FIG. 9, introduction of kinase-dead DGKζ partially restored IL-2 production from anergic CAR Tg Th1 cells. The DGK inhibitor R59022, which preferentially inhibits DGKα, also partially restored IL-2 production (FIG. 9).

The combination of kinase-dead DGKζz and R59022, to block both DGK isoforms, restored IL-2 production up to the level seen with exogenous PMA (FIG. 9). These results show that the component of T cell anergy that can be explained by a relative DAG deficiency (and thus be corrected by PMA) is mediated by DGKs, and that multiple DGK isoforms may contribute.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit, and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the concept, spirit, and scope of the invention as defined by the appended claims.

REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
Anandasabapathy et al., *Immunity*, 18:535-547, 2003.
Boussiotis et al., *Science*, 278:124-128, 1997.
Crespi et al., *Eur. J. Immunol.*, 32:2500-2509, 2002.
de Chaffoy de Courcelles et al., *J. Biol. Chem.*, 260:15762, 1985.
de Chaffoy de Courcelles et al., *J. Biol. Chem.*, 264:3274-3285, 1989.
Dower et al., *Nat. Immunol.*, 1:317-321, 2000.
Ebinu et al., *Blood*, 95:3199-3203, 2000.
Fields et al., *J. Immunol.*, 161:5268-5275, 1998.
Fields et al., *J. Mol. Med.*, 74:673-683, 1996.
Fields et al., *Science*, 271:1276-1278, 1996.
Frauwirth, et al., *J. Immunol.*, 167:4936-4941, 2001.
Gajewski et al., *Eur. J. Immunol.*, 25:1836-1842, 1995.
Gajewski et al., *J. Immunol.*, 143:15-22, 1989.
Gajewski et al., *J. Immunol.*, 166:3900-3907, 2001.
Houssa et al., *J. Biol. Chem.*, 274:6820-6822, 1999.
Huber, *Acta Cryst.*, B31, 108-113, 1975.
Jiang et al., *Biochem. Pharmacol.*, 59:763-772, 2000.
Kang et al., *Science*, 257:1134-1138, 1992.
Kanoh, et al, *Methods Enzymol.*, 209:162-172, 1992.
Lemaitre et al., *Biochem. J.*, 266:291-299, 1990.
Li et al., *Science*, 271:1272-1276, 1996.
Lin et al., *FEBS Lett.*, 467:184-188, 2000.
Manning et al., *J. Immunol.*, 159:4665-4675, 1997.
Nakamura et al., In: *Handbook of Experimental Immunology* (4th Ed.), Weir et al. (Eds), 1:27, Blackwell Scientific Publ., Oxford, 1987.
Nobe et al., *Br. J. Pharmacology*, 143:166-178, 2004.
Nunn et al., *Biochem. J.*, 243:809, 1987.
Nyberg-Hoffman et al., *Nat. Med.*, 5:955-957, 1999.
Outram et al, *Immunology*, 105:391-398, 2002.

PCT Appln. WO/84/03564
Peterson et al., *Eur. J. Immunol.*, 33(10):2687-2695, 2003.
Powell et al., *J. Immunol.*, 163:6631-6639, 1999.
Previati et al. *Cell Signal*, 6:393-403, 1994.
Ramsdell et al., *Science*, 246:1038-1041, 1989.
Rayter et al., *Embo J.*, 11:4549-4556, 1992.
Remington's Pharmaceutical Sciences, 18th Ed. Mack Printing Company, 1990.
Rivas et al., *J. Immunol.*, 167:3123-3128, 2001.
Sakane et al., *FEBS Lett.*, 255:409-413, 1989.
Sanjuan et al., *J. Cell Biol.*, 153:207-220, 2001.
Schaefer et al., *Cell Immunol.*, 214:110-122, 2001.
Schwartz, *Annu. Rev. Immunol.*, 21:305-334, 2003.
Sebzda et al., *Nat. Immunol.* 3:251-258, 2002.
Staveley-O'Carroll, et al., *Proc. Natl. Acad. Sci. USA*, 95:1178-83, 1998.
Swan, et al., *Embo J.*, 14:276-285, 1995.
Telander et al., *J. Immunol.*, 162:1460-1465, 1999.
Thomas and Glomset, *Biochem.*, 38:3310-3319, 1999.
Topham and Prescott, *J. Cell Biol.*, 152:1135-1143, 2001.
Tzachanis et al., *Nat. Immunol.*, 2:1174-1182, 2001.
van Blitterswijk et al., *Chem. Phys. Lipids*, 98:95-108, 1999.
Walsh et al., *J. Biol. Chem.*, 270:28647-28653, 1995.
Wan et al., *Proc. Natl. Acad. Sci. USA*, 97:13784-13789, 2000.
Wang et al., *J. Virol.*, 74:11296-11303, 2000.
Wei, *Nat. Struct. Biol.*, 4(9):699-703, 1997.
Younes et al., *J. Biol. Chem.*, 267:842-847, 1992.
Zhong et al., *J. Biol Chem.*, 277:31089-31098, 2002.
Zhong et al., *Nat. Immunol.*, 4:882-890, 2003.

What is claimed is:

1. A method of treating a subject having a condition that would benefit from up-regulation of an immune response comprising alleviating T cell anergy, wherein T cell anergy is alleviated by administering to the subject having a condition that would benefit from up-regulation of an immune response an effective amount of a inhibitor of diacylglycerol kinase (DGK)-α or DGK-ζ.

2. The method of claim 1, wherein the subject is a human.

3. The method of claim 1, wherein the inhibitor of DGK-α or DGK-ζ is selected from the group consisting of R59022, R59499, a dominant-negative DGK-α mutant, and a dominant-negative DGK-ζ mutant.

4. The method of claim 1, wherein the condition is cancer.

* * * * *